United States Patent [19]

Strong

[11] 4,254,268
[45] Mar. 3, 1981

[54] PROCESS FOR PREPARATION 4,5,6,7-TETRAHYDRO-7-OXOBENZO-[b]-THIOPHENES AND 1,2,3,4-TETRAHYDRO-4-OXO-1-NAPHTHALENES

[75] Inventor: Henry L. Strong, Somerset, N.J.

[73] Assignee: American Cyanamid Company, Stamford, Conn.

[21] Appl. No.: 918,299

[22] Filed: Jun. 22, 1978

Related U.S. Application Data

[63] Continuation of Ser. No. 834,014, Sep. 16, 1977, abandoned.

[51] Int. Cl.³ ............... C07D 333/54; C07C 103/127; C07C 127/19
[52] U.S. Cl. .................... 549/51; 260/326 A; 260/326 S; 560/28; 564/52; 564/166; 564/176; 564/211; 564/222
[58] Field of Search ............... 260/332.3 P, 332.3 R, 260/332.2 R, 332.2 A, 586 P, 586 F, 562 B, 562 P, 558 P, 553 A, 553 E, 326 A, 558 D, 559 R, 326 S; 560/28; 549/57, 51

[56] References Cited

U.S. PATENT DOCUMENTS

| | | | |
|---|---|---|---|
| 3,994,924 | 11/1976 | Asato | 260/332.3 P |
| 4,049,717 | 9/1977 | Asato | 424/322 |
| 4,053,484 | 10/1977 | Asato | 260/332.3 P |
| 4,134,899 | 1/1979 | Asato | 260/332.3 P |

OTHER PUBLICATIONS

Groggins, "Processes in Organic Synthesis",(1952), pp. 417–418.

*Primary Examiner*—Natalie Trousof
*Assistant Examiner*—L. Hendriksen
*Attorney, Agent, or Firm*—Harry H. Kline

[57] ABSTRACT

There is provided an oxidation process using potassium permanganate as oxidizing agent, for the preparation of certain animal growth promoters, namely, N-(4,5,6,7-tetrahydro-7-oxobenzo[b]thien-4-yl)amides, 4,5,6,7-tetrahydro-7-oxobenzo[b]-thien-4-ylureas, N-(1,2,3,4-tetrahydro-4-oxo-1-naphthyl)amides and 1,2,3,4-tetrahydro-4-oxo-1-naphthylureas, said process affording such compounds in markedly improved yields, and being readily suitable for scale-up.

8 Claims, No Drawings

PROCESS FOR PREPARATION 4,5,6,7-TETRAHYDRO-7-OXOBENZO-[b]-THIOPHENES AND 1,2,3,4-TETRAHYDRO-4-OXO-1-NAPHTHALENES

This is a continuation, of application Ser. No. 834,014, filed Sept. 16, 1977 now abandoned.

BACKGROUND OF THE INVENTION

Certain tetrahydro-7-oxobenzo[b]thien-4-ylurea compounds and certain tetrahydro-4-oxo-1-naphthylurea compounds are useful as growth-promoting agents for animals such as poultry, fur-bearing and farm animals. These compounds may be graphically illustrated and defined in general terms by formulae (A) and (B) as follows:

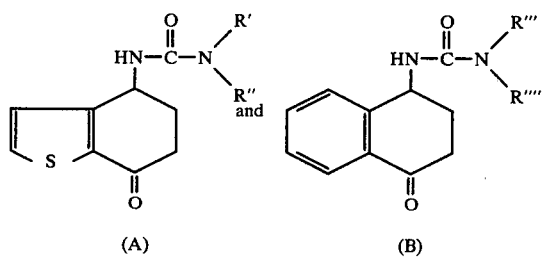

wherein the R groups R' to R'''' each represent hydrogen or some other moiety, selected to enhance the biological activity of said formulae (A) and (B) compounds.

The above oxo- compounds may be prepared from the corresponding urea compounds by oxidation of the ring-activated α-methylene group to a keto (oxo) group as schematically illustrated below:

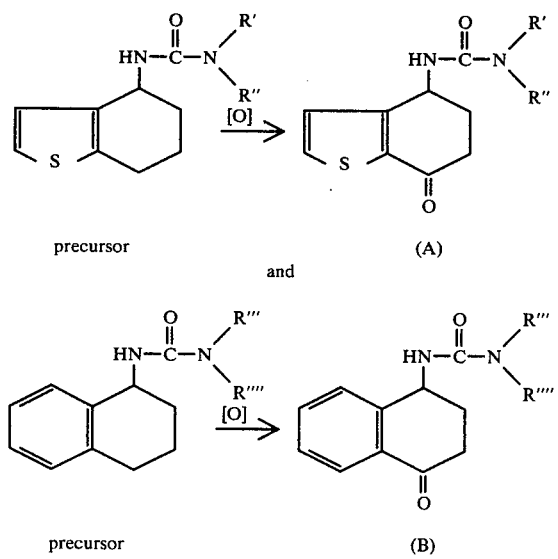

Alternatively, formulae (A) and (B) compounds, wherein the R groups R' to R'''' each are hydrogen, may be prepared from the corresponding oxo-amines of formulae (C) and (D) by reacting same with sodium or potassium cyanate, as schematically illustrated below:

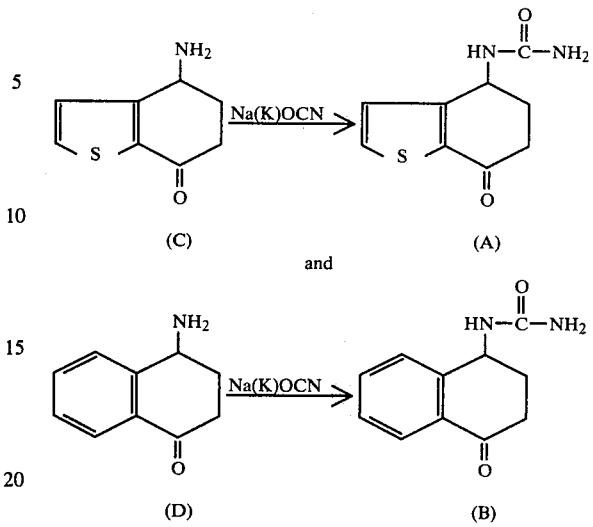

Substituted ureas of formulae (A) and (B) may be prepared by treating the amines of formulae (C) and (D) with an appropriately substituted isocyanate of formula: R'-NCO or with a carbamoyl halide of formula:

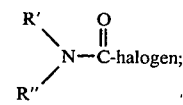

wherein R' and R" are as hereinabove-identified, and the halogen is bromine or chlorine.

The ring-activated α-methylene groups of the precursors of compounds of formulae (A) to (D) may be oxidized, using 2 to 8 mole equivalents, and preferably 4 to 8 mole equivalents, of an oxidizing agent selected from the group consisting of ceric ammonium nitrate, silver oxide or sodium bichromate at a temperature between about 0° C. and 100° C., and preferably 20° C. to 60° C., in a solvent selected from the group consisting of aqueous solutions of acetic acid, acetonitrile, tetrahydrofuran, dioxane, dimethoxyethane, diethylene glycol dimethyl ether, which may contain nitric acid, phosphoric acid or perchloric acid; or the oxidizing agent chromic anhydride in acetic anhydride followed by hydrolysis.

These oxidation reactions, while yielding the desired animal growth regulating compounds of formulae (A) and (B) or their respective precursors (C) and (D), leave much to be desired. In general, the above oxidation reactions afford the products usually in very low yields; large molar excesses of oxidizing agents (some of which are quite expensive) are needed; the reactions usually do not lend themselves readily for scale-up, and some of them represent fire and/or explosion hazards.

Clearly, there is a need for an oxidation process which would yield the above-described compounds of formulae (A) to (D) in satisfactory yields, and which would be free of the undesirable features of the above-referred-to oxidation processes.

It is, therefore, an object of the present invention to provide an improved oxidation process, employing potassium permanganate, for the preparation of the hereinabove generically identified tetrahydro-7-oxobenzo[b]thien-4-ylurea and tetrahydro-4-oxo-1- naphthylurea compounds of formulae (A) and (B), and their respective precursors, the compounds of formulae (C) and (D).

SUMMARY OF THE INVENTION

By the novel process of the present invention, ring-activated α-methylene groups in compounds of formulae (I) and (II):

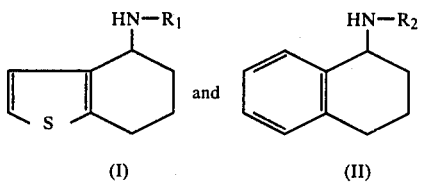

wherein $R_1$ and $R_2$ each are members selected from the group consisting of alkanoyl $C_1$-$C_7$, halogen-substituted alkanoyl $C_2$-$C_7$, carboalkoxy $C_1$-$C_7$,

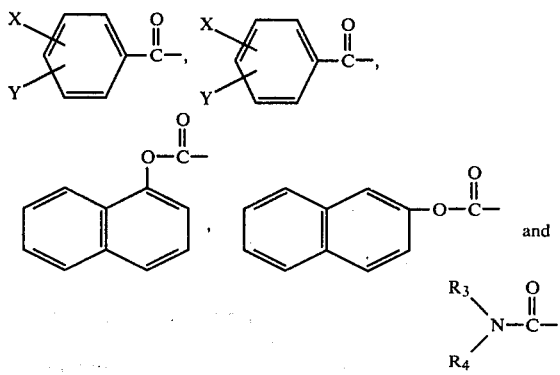

$R_3$ is a substituent selected from hydrogen and alkyl $C_1$-$C_4$; $R_4$ is a substituent selected from hydrogen, alkyl $C_1$-$C_8$, alkanoyl $C_2$-$C_4$, halogen-substituted alkanoyl $C_2$-$C_4$ and

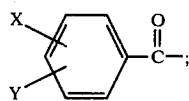

and when

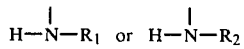

is each cyclized, each represents phthalimido; X and Y are selected from hydrogen, halogen, nitro, alkyl $C_1$-$C_4$ and alkoxy $C_1$-$C_4$; the racemic mixtures and the optical isomers thereof; may be conveniently prepared by reacting the same with 1.1 to 3.2 molar equivalents of potassium permanganate or other inorganic permanganates in a solvent selected from aqueous solutions of acetone, tert-butanol, pyridine, acetonitrile, glyme, and the like, in the pH range of 6 to below 11, and preferably 7 to 9. The pH of the reaction is maintained by the use of a buffer selected from magnesium sulfate, calcium sulfate, sodium bicarbonate, and the like, or by the periodic addition of an acid such as acetic acid, as required. The oxidation reactions are carried out in the temperature range of from about 0° C. to about 50° C., and preferably 10° C. to 20° C., for a period of time from about 3 hours to about 16 hours, or until the reaction is essentially complete. The products are obtained in satisfactory yields. The reaction is less hazardous than many other methods previously used, and may be scaled-up successfully.

The high yields obtained in these permanganate oxidations is surprising, especially in view of the findings of Schecter et al. [*Journal of the American Chemical Society*, 86, 1701 and 1706 (1964)], who have found that benzyl amines are oxidized by buffered permanganate. Waters and Littler in Wiberg's, "Oxidation in Organic Chemistry," Volume 5A, pages 60–61 (1965), also discuss the ease with which nitrogen-containing functional groups are oxidized with other comparable oxidizing agents. Therefore, because of this general susceptibility of nitrogen-containing functional groups to oxidation, the results obtained with buffered permanganate in the process hereindefined are unexpected.

The above oxidation reaction may be graphically illustrated as follows:

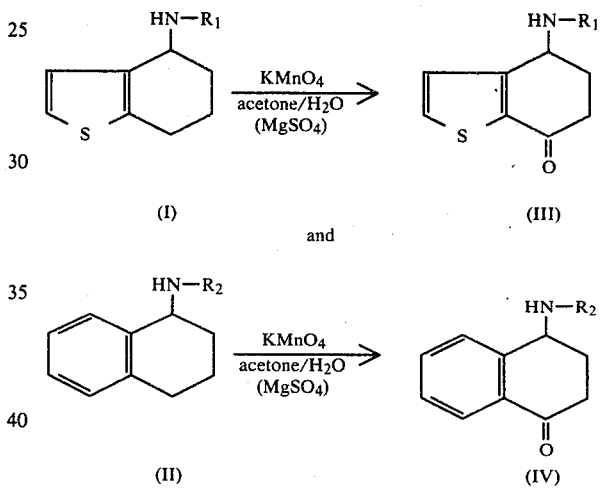

wherein $R_1$ and $R_2$ are as hereinabove defined.

Thus, for instance, the animal growth-promoting agent, 4,5,6,7-tetrahydro-7-oxobenzo[b]thien-4-ylurea of formula (A) may be conveniently prepared from N-(4,5,6,7-tetrahydrobenzo[b]thien-4-yl)acetamide, utilizing the above novel oxidation process as follows:

One molar equivalent of N-(4,5,6,7-tetrahydrobenzo[b]thien-4-yl)acetamide is oxidized in aqueous acetone at 10° C. to 15° C. with 2.66 moles of potassium permanganate in the pH range of 7 to 9 in the presence of magnesium sulfate buffer for a period of time from about 3 to 5 hours to afford N-(4,5,6,7-tetrahydro-7-oxobenzo[b]thien-4-yl)acetamide. The thus-obtained oxo-acetamide is hydrolyzed in aqueous hydrochloric acid to the corresponding amine. This amine is then reacted with sodium or potassium cyanate in an aqueous medium at about pH 6.5, and at a temperature of about 60° C. to 65° C., to afford the animal growth-promoting 4,5,6,7-tetrahydro-7-oxobenzo[b]thien-4-ylurea of formula (A). Oxidation of 4,5,6,7-tetrahydrobenzo[b]thien-4-ylurea under reaction conditions, similar to those described above, also affords the aforesaid urea of formula (A). The above reaction sequence may be graphically illustrated as follows:

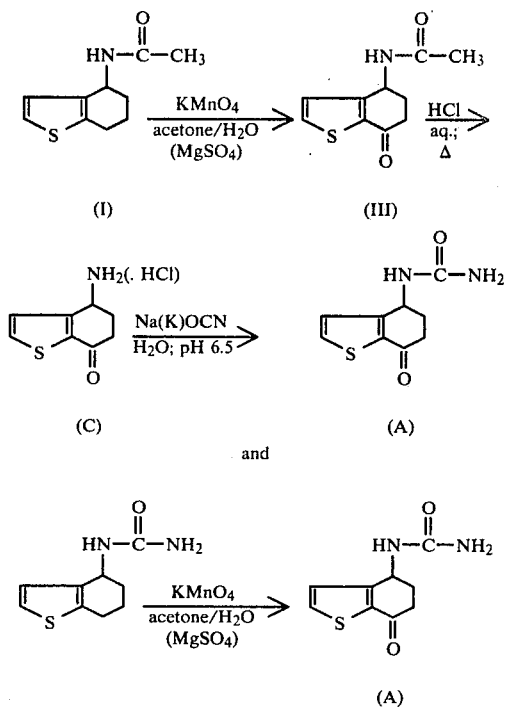

Substituted ureas of formula (A) may be prepared by treating the amine of formula (C) with the appropriately substituted isocyanate of formula: R'-NCO or with a carbamoyl chloride of formula:

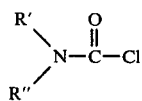

in an aprotic solvent in the presence of an acid acceptor at a temperature range of from about 0° C. to about 100° C.

The animal growth-promoting compounds of formula (B) may also be prepared, conveniently, by the above novel oxidation process. Thus, N-(1,2,3,4-tetrahydro-1-naphthyl)-acetamide of formula (II) is oxidized with potassium permanganate to the corresponding N-(1,2,3,4-tetrahydro-4-oxo-1-naphthyl)acetamide of formula (IV).

Next, the amide is hydrolyzed in dilute hydrochloric acid to the amine of formula (D), followed by reaction of said amine with sodium or potassium cyanate, or with the appropriately substituted isocyanate of formula: R'''-NCO, or with a carbamoyl chloride of formula:

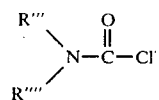

to afford an unsubstituted-, monosubstituted-, or disubstituted-urea of formula (B), respectively.

As stated above, formulae (A) and (B) compounds are useful as growth-promoting agents for animals such as poultry, fur-bearing and farm animals.

In practice, a growth-promoting amount of a formula (A) or formula (B) compound is administered to a host animal in or with the animal's feed. Said compound may also be administered as a subcutaneous implant under the skin of said animal or as a parenteral injection.

The present invention is further illustrated by the non-limiting examples set forth below.

EXAMPLE 1

Preparation of N-(4,5,6,7-Tetrahydro-7-oxobenzo[b]thien-4-yl)acetamide

Acetone (200 ml), N-(4,5,6,7-tetrahydrobenzo[b]-thien-4-yl) acetamide (9.75 g, 0.05 mol) and magnesium sulfate (21.0 g, 0.17 mol) are mixed, stirred and cooled to 10° C. Next, 150 ml of an aqueous potassium permanganate solution (prepared from 21.0 g, 0.133 mol of potassium permanganate and 200 ml of water) is added over 15 minutes to the above mixture, and the whole stirred for 3 hours. After 3 hours reaction time, analysis of the mixture by high pressure liquid chromatography (HPLC) indicates the reaction to be incomplete. The remainder of the above potassium permanganate solution (~50 ml) is added and the reaction mixture stirred for two more hours. Isopropanol (20 ml) is then added, the reaction mixture stirred overnight, and filtered. HPLC analysis of the filtered solution indicates a 73.6% yield of title product, and also the presence of 2% of starting material.

The acetone is removed from the above solution in vacuo at 40° C. There is obtained approximately 200 ml of an aqueous solution of title product. This solution can be used as is for the preparation of 4,5,6,7-tetrahydro-7-oxobenzo[b]thien-4-ylurea, an animal growth regulant.

By the above procedure, but substituting N-(4,5,6,7-tetrahydrobenzo[b]thien-4-yl)benzamide or N-(4,5,6,7-tetrahydrobenzo[b]thien-4-yl) 4-chlorobenzamide for N-(4,5,6,7-tetrahydrobenzo[b]thien-4-yl)acetamide, N-(4,5,6,7-tetrahydro-7-oxobenzo[b]thien-4-yl)benzamide, or N-(4,5,6,7-tetrahydro-7-oxobenzo[b]thien-4-yl) 4-chlorobenzamide, can be obtained, respectively.

EXAMPLES 2 to 6

Preparation of N-(4,5,6,7-Tetrahydro-7-oxobenzo[b]thien-4-yl)acetamide.

General Procedure

N-(4,5,6,7-tetrahydrobenzo[b]thien-4-yl)acetamide and magnesium sulfate are dissolved in a mixture of acetone and water. The solution is stirred and its temperature adjusted to the desired range. Next, potassium permanganate is added in small portions over a period of time. The oxidation reaction is run for a period of time, is then quenched with isopropanol and worked up as in Example 1. Product yields are determined by HPLC.

The amounts of reaction components used, the time and temperature variables and the product yields of the individual examples are summarized in Table I below.

TABLE I

Evaluation of the Effect of Reaction Variables on Product Yields

| Example | Starting Material g | Starting Material Mole | MgSO4 g | Acetone ml | H2O ml | KMnO4 Addition g | KMnO4 Addition Time | Reaction Time | Reaction Temperature °C. | Product Yield % |
|---|---|---|---|---|---|---|---|---|---|---|
| 2 | 9.75 | 0.05 | 21.0 | 200 | 200 | 21.0 | 10 minutes | 6 hours | 10–15 | 70.5 |
| 3 | 9.75 | 0.05 | 8.81 | 112.5 | 37.5 | 21.0 | 1 hour | 12 hours | 10 | 75.2 |
| 4 | 9.75 | 0.05 | 8.81 | 75 | 75 | 25.0 | 1 hour | 3 hours | 10 | 69.0 |
| 5 | 9.75 | 0.05 | 8.81 | 112.5 | 37.5 | 25.0 | 2 hours | 13 hours | 10 | 73.0 |
| 6 | 9.75 | 0.05 | 10.0 | 75 | 75 | 21.0 | 1.5 hours | 4 hours | 50 | 60.1 |

EXAMPLE 7

Preparation of 4,5,6,7-Tetrahydro-7-oxobenzo[b]thien-4-ylurea from the Corresponding Ketoamide of Example 1

Concentrated hydrochloric acid (200 ml) is added to the aqueous solution of N-(4,5,6,7-tetrahydro-7-oxobenzo[b]thien-4-yl)acetamide of Example 1 (~200 ml, 7.66 g, 0.0368 mol). The solution is heated at reflux for 3 hours, decolorized with activated charcoal, cooled down and filtered. The pH of the thus-obtained solution is adjusted to 6.5 with 50% sodium hydroxide, and potassium cyanate (5.0 g, 0.062 mol) is added. The reaction mixture is stirred for 0.5 hour at room temperature, then for one hour at 65° C., and finally overnight at room temperature. The reaction mixture is then filtered, the isolated solids washed with water and dried at 60° C. in vacuo. There is obtained 5.1 g of title product, 90% pure by analysis.

By the above procedure, but substituting N-(4,5,6,7-tetrahydro-7-oxobenzo[b]thien-4-yl)benzamide or N-(4,5,6,7-tetrahydro-7-oxobenzo[b]thien-4-yl) 4-chlorobenzamide, the above title compound can be obtained.

EXAMPLE 8

Large Scale Preparation of 4,5,6,7-Tetrahydro-7-oxobenzo[b]-thien-4-ylurea

Acetone (2250 ml), water (750 ml), N-(4,5,6,7-tetrahydrobenzo[b]thien-4-yl)acetamide (195.3 g, 1.0 mol) and magnesium sulfate (210.0 g, 1.744 mol) are mixed and stirred for 0.5 hour at room temperature, and then the solution is cooled to 10° C. Potassium permanganate (500.0 g, 3.168 mol) is added in 20–21 g portions with stirring over a 2-hour period while the reaction temperature is maintained at 10°–15° C. During the last half hour of permanganate addition, the reaction mixture exotherms to 20°–21° C., is rapidly cooled down to 10°–15° C. and is maintained at 10°–15° C. until the permanganate addition is completed. The reaction mixture is then stirred 4 hours at room temperature, and at that time is found to be incomplete by HPLC. Stirring is continued overnight at room temperature, and after that time the reaction is found to be about 95% complete by HPLC. Filter aid (50 g) is added, the reaction mixture stirred 0.5 hour and filtered. The filter cake is washed with acetone (4×1000 ml), then extracted with acetone (1500 ml). The above filtrate, the acetone washings and extract are combined and analyzed by HPLC. The analysis indicates the product yield to be 143.42 g, 68.6% of theory. Some starting material (8.4 g, 4.3%) is also present in the solution.

Next, the acetone is removed from the solution in vacuo at 40°–45° C., and the volume of the remaining solution adjusted to 1200 ml with water. Concentrated hydrochloric acid (250 ml) is added, the solution heated to reflux (in about 50 minutes) and refluxed for 5 hours. After 5 hours, HPLC analysis indicates the hydrolysis to be 98% complete. The reaction mixture is cooled to room temperature, activated charcoal (20 g) and filter aid (40 g) are added, and the mixture filtered. The pH of the filtrate is adjusted with 50% sodium hydroxide (~150 ml) to 6.6, while the temperature is maintained at about 25° C. Next, sodium cyanate (82.0 g, 1.26 mol) is added in small portions at room temperature over a one-hour period, the reaction mixture is then heated at 60°–65° C. for one hour, and finally cooled to room temperature and filtered. The isolated product is washed with water (3000 ml), methanol (500 ml) and dried. There is obtained 135.9 g (overall yield: 64.6%) product, (purity: 95.3%) melting point 246.5°–248.5° C. A 50 g sample is recrystallized from methanol (500 ml). Yield: 48.14 g, (purity: 97%) melting point 249.5°–250.5° C. (dec.).

EXAMPLES 9 to 16

Evaluation of the Effect of pH on the Product Yields of the Oxidation Reaction

General Procedure

N-(4,5,6,7-tetrahydrobenzo[b]thien-4-yl)acetamide is dissolved in a mixture of acetone and water. The solution is stirred and its temperature adjusted to the desired range. Potassium permanganate is added, and the reaction is run for a period of time while the pH of the reaction mixture is maintained at a predetermined value. Finally, the reaction is quenched with isopropanol and worked up as in Example 1. Product yields are determined by HPLC.

The amounts of reaction components used, the time, temperature and pH variables, and the product yields of the individual examples are summarized in Table II below.

TABLE II

Evaluation of the Effect of pH on Product Yields

| Example | Starting Material g | Starting Material Mole | Acetone; ml | Water; ml | KMnO4 Addition g | KMnO4 Addition Time | pH | Reaction Temperature °C. | Time; Hours | Yield % |
|---|---|---|---|---|---|---|---|---|---|---|
| 9 | 9.75 | 0.05 | 300 | 100 | 21 | | 5 | 10 | 6.5 | 56.66 |
| 10 | 9.75 | 0.05 | 300 | 100 | 21 | | 6 | 10 | 6.5 | 70.0 |
| 11 | 9.75 | 0.05 | 112.5 | 37.5 | 25 | 2 hours | 7 | 10–15 | 8 | 71.1 |
| 12 | 9.75 | 0.05 | 300 | 100 | 21 | | 8 | 10 | 5 | 77.4 |

TABLE II-continued

Evaluation of the Effect of pH on Product Yields

| Example | Starting Material g | Mole | Acetone; ml | Water; ml | KMnO4 Addition g | Time | pH | Reaction Temperature °C. | Time; Hours | Yield % |
|---|---|---|---|---|---|---|---|---|---|---|
| 13 | 9.75 | 0.05 | 300 | 100 | 21 | | 9 | 10 | 5 | 73.3 |
| 14 | 9.75 | 0.05 | 300 | 100 | 21 | | 10 | 10 | 5 | 67.6 |
| 15 | 9.75 | 0.05 | 300 | 100 | 21 | | 11 | 10 | 5 | 57.2 |
| 16 | 9.75 | 0.05 | 300 | 100 | 21 | | 12 | 10 | 5 | 42.5 |

EXAMPLES 17 to 19

Evaluation of the Effect of Various Buffers on the Product Yields of the Oxidation Reaction N-(4,5,6,7-tetrahydrobenzo[b]thien-4-yl)acetamide (9.75 g, 0.05 mol) is dissolved in a mixture of acetone (300 ml) and water (100 ml). Next, the appropriate buffer is added, the temperature of the solution adjusted to the desired range, and potassium permanganate (25 g) is added. The reaction is run for a period of time, and then worked up as in Example 1. Product yields are determined by HPLC. The experimental details are summarized in Table III below.

TABLE III

Evaluation of the Effect of Various Buffers on the Product Yields of the Oxidation Reaction

| Example | Buffer; g | Reaction Temperature °C. | Time | pH | Yield % |
|---|---|---|---|---|---|
| 17 | CH3COOH 13.6 | 10-15 | overnight* | 6.4 | 78.5 |
| 18 | NaHCO3 20.0 | 10 then room temperature | 3 hours then overnight | 10.4 | 74.2 |
| 19 | CaSO4 20.0 | 10 then room temperature | 3 hours then overnight | 8.2 | 73.5 |

*After having run overnight, potassium permanganate (5.0 g) and acetic acid (2.0 g) are added to the mixture and the reaction is run 4 hours at 10°-15° C.

EXAMPLES 20 to 28

Evaluation of the Effects of Various Solvents, Used as Reaction Media, on Product Yields of the Oxidation Reaction

General Procedure

N-(4,5,6,7-tetrahydrobenzo[b]thien-4-yl)acetamide (9.75 g, 0.05 mol), magnesium sulfate (21.0 g) and the reaction solvent(s) selected are mixed, stirred and cooled to 10° C. Potassium permanganate is added, and the oxidation reaction run for a period of time. Then more potassium permanganate is added if needed, and the reaction run for an additional period of time. The experiments are worked up as in Example 1. Product yields are determined by HPLC.

The experimental details are summarized in Table IV below.

TABLE IV

Evaluation of the Effect of Various Solvents and Solvent Mixtures on the Product Yield of the Oxidation Reaction

| | Solvent | | KMnO4 Addition and Reaction Conditions | | | | | | Yield % |
|---|---|---|---|---|---|---|---|---|---|
| | | | First Addition | | Second Addition | | Third Addition | | |
| Example | I (200 ml) | II (200 ml) | g - Time | Rx Time-Temperature | g - Time | Rx Time-Temperature | g - Time | Rx Time - Temperature | |
| 20 | acetone | — | 21 g 15 min. | 6 hours 10° C. | — | — | — | — | 31.5 |
| 21 | pyridine | — | 21 g 15 min. | 4 hours 10° C. overnight-room temperature | — | — | — | — | 40.8 |
| 22 | acetic anhydride | — | 21 g 15 min | 4 hours 10° C. overnight**-room temperature | — | — | — | — | 20.8 |
| 23 | pyridine | H2O | 21 g 15 min. | 4 hours 10° C. overnight**-room temperature | — | — | — | — | 75.8 |
| 24 | t-butanol | H2O | 21 g 15 min. | 6 hours 10° C. | — | — | — | — | 58.1 |
| 25 | diethyl ketone | H2O | 21 g 15 min. | 4 hours 10° C. | 21 g 4 hours | 10° C. | 21 g 3 hours | overnight**-room temperature | 26.2 |
| 26 | CH2Cl2 | H2O | 21 g 15 min. | 5 hours 10° C. | 21 g 15 min. | 3 hours 10° C. | 10 g | overnight**-room temperature | 16.0 |
| 27* | benzene | H2O | 11 g 15 min. | 4 hours 10° C. | 10 g 15 min. | overnight**-room | — | — | 16.6 |

TABLE IV-continued

Evaluation of the Effect of Various Solvents and Solvent Mixtures on the Product Yield of the Oxidation Reaction

| | Solvent | | KMnO$_4$ Addition and Reaction Conditions | | | | | | |
|---|---|---|---|---|---|---|---|---|---|
| | | | First Addition | | Second Addition | | Third Addition | | |
| Example | I (200 ml) | II (200 ml) | g - Time | Rx Time-Temperature | g - Time | Rx Time-Temperature | g - Time | Rx Time - Temperature | Yield % |
| 28 | ethyl acetate | H$_2$O | 21 g 15 min. | 3 hours 10° C. | 10.5 g 30 min. | temperature 2 hours 10° C. | 10.5 g 30 min. | over*** weekend-room temperature | 21.1 |

*One gram benzyl triethylammonium chloride is added as phase transfer catalyst.
**12 hours
***50 hours

EXAMPLE 29

Preparation of 4,5,6,7-Tetrahydro-7-oxobenzo[b]thien-4-ylurea by Permanganate Oxidation from the Corresponding Thienylformamide N-(4,5,6,7-tetrahydrobenzo[b]thien-4-yl)formamide (6.0 g, 77.9% pure), magnesium sulfate (10 g), acetone (100 ml) and water (100 ml) are mixed, stirred and the solution cooled to 10° C. Potassium permanganate (11.0 g) is added over 5 minutes, and the reaction mixture stirred for 4.5 hours. Ethanol (20 ml) is added and the reaction mixture stirred overnight. The mixture is then filtered, the filter cake washed with acetone and water. Filtrate and washings are combined and the acetone stripped from the solution in vacuo.

Concentrated hydrochloric acid (25 ml) is added to the aqueous solution, and the mixture heated at reflux for 2 hours. The solution is cooled to room temperature, its pH adjusted to 6.5 with sodium hydroxide solution. Sodium cyanate (2.1 g) is added, the mixture stirred 0.5 hour at room temperature, an hour at 65° C., and is then cooled to room temperature and filtered. The filter cake is washed with water and dried at 60° C. in vacuo to afford 3.1 g (57.4%) of title product.

EXAMPLE 30

Preparation of 4,5,6,7-Tetrahydro-7-oxobenzo[b]thien-4-ylurea by Permanganate Oxidation from the Corresponding Thienylurea Acetone (200 ml), water (200 ml) and 4,5,6,7-tetrahydrobenzo[b]thien-4-ylurea (10.0 g) are mixed, stirred and cooled to 10° C. Potassium permanganate (21.0 g) is added over 5 minutes, and the reaction mixture stirred for 5 hours while the pH of the reaction mixture is maintained at 7 to 8 with aqueous acetic acid. The pH of the reaction mixture is then adjusted to 4, and sulfur dioxide is bubbled through, until no MnO$_2$ is found in the mixture. The mixture is stirred overnight. Two solid phases form and are filtered separately, the filter cakes washed with water and dried at 60° C. in vacuo. There is obtained 1.1 g solid from the top phase and 2.7 g from the bottom phase, respectively.

The acetone is stripped from the mother liquor in vacuo, the aqueous slurry is filtered, the cake washed with water, and dried at 60° C. in vacuo to afford 2.01 g solid. Analyses of the above fractions indicate an over-all yield of 43% of title product.

EXAMPLE 31

Preparation of (1,2,3,4-Tetrahydro-4-oxo-1-naphthyl)urea by a Two-Step Process

1. Preparation of (1,2,3,4-Tetrahydro-4-oxo-1-naphthyl)-acetamide Intermediate

N-(1,2,3,4-tetrahydro-1-naphthyl)acetamide (19.0 g, 0.1 mol), magnesium sulfate (11.08 g), acetone (300 ml) and water (100 ml) are mixed, stirred and cooled to 10° C. The pH of the solution is 7.9. Potassium permanganate (26.44 g) is added, and the reaction mixture stirred at 10° C. for 7 hours. Isopropanol (50 ml) is added and the reaction mixture stirred overnight at room temperature. Next, a small amount of sodium sulfite is added and the mixture stirred about one hour to destroy the remaining permanganate. Filter aide is added, the mixture filtered, and the cake washed with acetone (4×50 ml). HPLC analysis of combined filtrate and washings indicate a 96.5% yield.

Acetone is removed from the solution in vacuo at about 50° C. Concentrated hydrochloric acid (170 ml of 12 N) is added to the remaining aqueous solution (170 ml), the mixture heated at reflux for 3 hours, then cooled to room temperature. Activated charcoal (2 g) and filter aide (4 g) are added, the mixture stirred for 0.5 hour, and is then filtered through a bed of filter aide. The filter cake is washed with water and filtrate, and washings are combined.

2. Preparation of the Title Product

The pH of the above solution is adjusted to 6.5 with 50% sodium hydroxide (∼120 ml). Sodium cyanate (12 g) is added next, the reaction mixture stirred at room temperature for one hour, then at 60°-65° C. for one hour, cooled down and finally chilled in an ice bath and filtered. The filter cake is washed with water, dried at 60° C. to afford 19.0 g (68.3%) of title product, melting point 234°-235° C.

EXAMPLE 32

Mouse Growth Regulant Tests

CFI female mice from Carworth Farm are received when they are six weeks old. They are housed ten to a cage in air-conditioned rooms (72° F. to 76° F.) with automatically controlled lights, 14 hours on and 10 hours off. The basal diet used in these studies is Purina Laboratory Chow (see description below), which is supplied ad libitum. Water is also allowed ad libitum.

Thirteen days after arrival, the mice are weighed in groups of ten and assigned at random to the different treatments. The concentration of the different compounds in the diet is indicated in the following Table. Twelve days later, the mice are weighed again and the experiment terminated. At least ten cages (100 mice) of untreated controls are included in each test. Test data are provided in Table V below, wherein data are reported as percent weight gain over controls. The following is a description of the diet to which the growth-promoting compounds are added.

| DIET | |
|---|---|
| GUARANTEED ANALYSIS | |
| Crude protein not less than | 23.0% |
| Crude fat not less than | 4.5% |
| Crude fiber not more than | 6.0% |
| Ash not more than | 9.0% |
| Meat and bone meal, dried skimmed milk, wheat germ meal, fish meal, animal liver meal, dried beet pulp, ground extruded corn, ground oat groats, soybean meal, dehydrated alfalfa meal, cane molasses, animal fat preserved with BHA, vitamin $B_{12}$ supplement, calcium pantothenate, choline chloride, folic acid, riboflavin supplement, brewers' dried yeast, thiamin, niacin, vitamin A supplement, D activated plant sterol, vitamin E supplement, calcium carbonate, dicalcium phosphate, iodized salt, ferric ammonium citrate, iron oxide, manganous oxide, cobalt carbonate, copper oxide, zinc oxide. | |

TABLE V

Effectiveness of 4,5,6,7-Tetrahydro-7-oxobenzo[b]thien-4-ylurea as Animal Growth Promoter Reported as Percent Weight Gain Over Control Using Mice as the Test Animal. The Data are Averages of Five Cages at Each Level of Drug.

| Compound | Rate ppm in Diet | % Weight Gain Over Controls |
|---|---|---|
| Example 8 Crude | 6 | 3.3 |
| | 12 | 34.9 |
| | 25 | 41.1 |
| | 50 | 65.9 |
| Example 8 Recrystallized | 6 | 11.4 |
| | 12 | 18.8 |
| | 25 | 53.3 |
| | 50 | 41.2 |

I claim:

1. A process for the preparation of a compound of the formula:

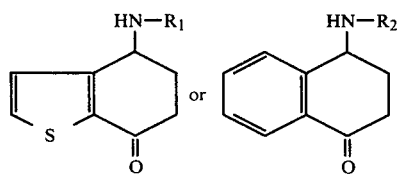

wherein $R_1$ and $R_2$ are each a substituent selected from the group consisting of alkanoyl $C_1$-$C_7$, halogen-substituted

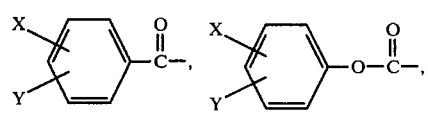

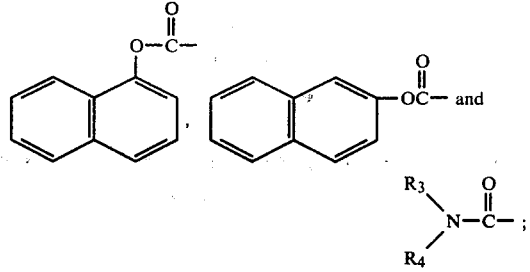

$R_3$ is a substituent from hydrogen and alkyl $C_1$-$C_4$; $R_4$ is a substituent selected from hydrogen, alkyl $C_1$-$C_8$, alkanoyl $C_1$-$C_4$, halogen-substituted alkanoyl $C_2$-$C_4$ and

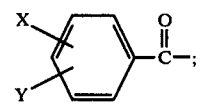

and when

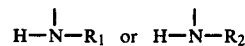

is each cyclized, each represents phthalimido; X and Y are selected from hydrogen, halogen, nitro, alkyl $C_1$-$C_4$ and alkoxy $C_1$-$C_4$; the racemic mixtures and the optical isomers thereof, consisting essentially in the steps of: oxidizing a compound of the formula:

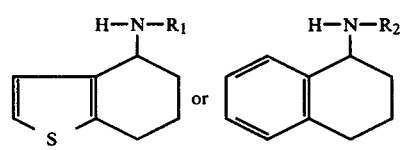

wherein $R_1$ and $R_2$ are each a substituent as hereinabove defined; with 2.5 to 3.2 molar equivalents of potassium permanganate at a temperature ranging from 0° C. to 50° C., in a solvent selected from aqueous solutions of acetone, tert-butanol, pyridine and acetonitrile, in the pH of from 6 to below 11, in the presence of a buffer selected from magnesium sulfate, calcium sulfate, sodium bicarbonate and acetic acid, for a period of time sufficient to essentially complete the reaction and recovering a compound of the formula:

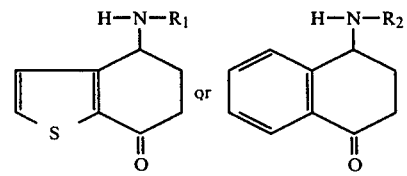

where $R_1$ and $R_2$ are as defined hereinabove.

2. The process according to claim 1, wherein $R_1$ and $R_2$ each are selected from alkanoyl C-hd 1-$C_2$, and

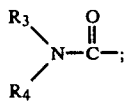

$R_3$ and $R_4$ each are hydrogen; the compounds are oxidized with 2.5 to 3.2 molar equivalents of potassium permanganate at a temperature ranging from 10° C. to 20° C., in a solvent selected from aqueous solutions of acetone, tert-butanol and pyridine, in the pH range of 7 to 9, in the presence of a buffer selected from magnesium sulfate, calcium sulfate, sodium bicarbonate and acetic acid; for a period of time of from three to sixteen hours.

3. The process according to claim 1, wherein the compound to be oxidized is N-(4,5,6,7-tetrahydrobenzo[b]thien-4-yl)formamide.

4. The process according to claim 1, wherein the compound to be oxidized is N-(4,5,6,7-tetrahydrobenzo[b]thien-4-yl)acetamide.

5. The process according to claim 1, wherein the compound to be oxidized is 4,5,6,7-tetrahydrobenzo[b]thien-4-ylurea.

6. The process according to claim 1, wherein the compound to be oxidized is N-(1,2,3,4-tetrahydro-1-naphthyl)-formamide.

7. The process according to claim 1, wherein the compound to be oxidized is N-(1,2,3,4-tetrahydro-1-naphthyl)-acetamide.

8. The process according to claim 1, wherein the compound to be oxidized is 1,2,3,4-tetrahydro-1-naphthylurea.

* * * * *

UNITED STATES PATENT AND TRADEMARK OFFICE
CERTIFICATE OF CORRECTION

PATENT NO. : 4,254,268
DATED : March 3, 1981
INVENTOR(S) : Henry Lee Strong

It is certified that error appears in the above-identified patent and that said Letters Patent is hereby corrected as shown below:

Column 14, line 15, between "substituent" and "from" insert -- selected --.

Column 14, last line, cancel "C-hd 1-$C_2$," and substitute instead -- $C_1$-$C_2$ --.

Signed and Sealed this

Fifteenth Day of March 1983

[SEAL]

Attest:

Attesting Officer

GERALD J. MOSSINGHOFF
Commissioner of Patents and Trademarks